US011298348B2

(12) United States Patent
Richard et al.

(10) Patent No.: US 11,298,348 B2
(45) Date of Patent: Apr. 12, 2022

(54) COMBINATION TREATMENT OF SARCOGLYCANOPATHIES

(71) Applicants: INSERM (INSTITUT NATIONAL DE LA SANTE ET DE LA RECHERCHE MEDICALE), Paris (FR); UNIVERSITE D'EVRY-VAL-D'ESSONNE, Evry (FR); GENETHON, Evry (FR); UNIVERSITA 'DEGLI STUDI DI PADOVA, Padua (IT)

(72) Inventors: Isabelle Richard, Evry (FR); Dorianna Sandona, Padua (IT)

(73) Assignees: INSERM (INSTITUT NATIONAL DE LA SANTE ET DE LA RECHERCHE MÉDICALE), Paris (FR); UNIVERSITE D'EVRY-VAL-D'ESSONNE, Evry (FR); GENETHON, Evry (FR); UNIVERSITA 'DEGLI STUDI DI PADOVA, Padua (IT)

(*) Notice: Subject to any disclaimer, the term of this patent is extended or adjusted under 35 U.S.C. 154(b) by 0 days.

(21) Appl. No.: 16/960,503

(22) PCT Filed: Jan. 10, 2019

(86) PCT No.: PCT/EP2019/050585
§ 371 (c)(1),
(2) Date: Jul. 7, 2020

(87) PCT Pub. No.: WO2019/138012
PCT Pub. Date: Jul. 18, 2019

(65) Prior Publication Data
US 2021/0059999 A1 Mar. 4, 2021

(30) Foreign Application Priority Data
Jan. 11, 2018 (EP) .................... 18305018

(51) Int. Cl.
*A61K 31/47* (2006.01)
*A61P 21/00* (2006.01)
*A61K 31/427* (2006.01)

(52) U.S. Cl.
CPC ............ *A61K 31/47* (2013.01); *A61K 31/427* (2013.01); *A61P 21/00* (2018.01)

(58) Field of Classification Search
CPC ........ A61K 31/47; A61K 31/427; A61P 21/00
See application file for complete search history.

(56) References Cited

FOREIGN PATENT DOCUMENTS

| WO | WO 2004/111014 A1 | 12/2004 |
|---|---|---|
| WO | WO 2006/101740 A2 | 9/2006 |
| WO | 2014/086687 | * 6/2014 |
| WO | WO 2014/086687 A1 | 6/2014 |

OTHER PUBLICATIONS

Bartoli et al., "Mannosidase I Inhibition Rescues the Human Alpha-Sarcoglycan R77C Recurrent Mutation", Hum Mol Genet. May 1, 2008;17(9):1214-21.
Bianchini et el., "Unveiling the Degradative Route of the $V_{247}M$ a-sarcoglycan Mutant Responsible for LGMD-2D", Hum Mol Genet, Jul. 15, 2014;23(14):3746-58.
Boinot et al., "Searching for Combinations of Small-Molecule Correctors to Restore F508del-Cystic Fibrosis Transmembrane Conductance Regulator Function and Processing", Journal of Pharma Cology and Experimental Therapeutics, vol. 350, No. 3, Jun. 26, 2014 (Jun. 26, 2014), pp. 624-634.
Carotti et al., "Repairing folding-defective [alpha]-sarcoglycan mutants by CFTR correctors, a potential therapy for limb-girdle muscular dystrophy 2D", Human Molecular Genetics, vol. 27, No. 6, Jan. 16, 2018 (Jan. 16, 2018), pp. 969-984.
Carrie et al., " Mutational Diversity and Hot Spots in the Alpha-Sarcoglycan Gene in Autosomal Recessive Muscular Dystrophy ($LGMD_2D$)", J Med Genet. Jun. 1997;34(6):470-5.
Duggan et al., "Mutations in the Sarcoglycan Genes in Patients With Myopathy", N Engl Med. Feb. 27, 1997;336(9):618-24.
Farinha et al., "Revertants, Low Temperature, and Correctors Reveal the Mechanism of F508del-CFTR Rescue by VX-809 and Suggest Multiple Agents for Full Correction", Chemistry and Biology., vol. 20, No. 7, Jul. 1, 2013 (Jul. 1, 2013), pp. 943-955.
Gastaldello et al., "Inhibition of Proteasome Activity Promotes the Correct Localization of Disease-Causing Alpha-Sarcoglycan Mutants in HEK-293 Cells Constitutively Expressing Beta-, Gamma-, and Delta-Sarcoglycan", Am J Pathol. Jul. 2008;173(1):170-81.
Kirschner et al., "Sarcoglycanopathies", Handb Clin Neurol. 2011;101:41-6.
Loo et al., "Corrector-mediated rescue of misprocessed CFTR mutants can be reduced by the P-glycoprotein drug pump", Biochemical Pharmacology, Elsevier, US, vol. 83, No. 3, Nov. 18, 2011 (Nov. 18, 2011), pp. 345-354.
Nigro et al., "Genetic Basis of Limb-Girdle Muscular Dystrophies: The 2014 Update", Acta Myol. May 2014;33(1):1-12.

(Continued)

*Primary Examiner* — D Margaret M Seaman
(74) *Attorney, Agent, or Firm* — Knobbe, Martens, Olson & Bear LLP

(57) ABSTRACT

Sarcoglycanopathies are autosomal recessive diseases caused by mutations in the one of the genes coding for any sarcoglycans (SG). The inventors previously showed that the application of small molecules developed to rescue ΔF508-CFTR trafficking, and known as CFTR correctors, improved the maturation of several α-sarcoglycan mutants that were consequently rescued at the plasma membrane (WO 014086687). Now, the inventors show that some specific CFTR correctors provide additive and even synergic effect when administered in combination.

4 Claims, 4 Drawing Sheets

(56) References Cited

OTHER PUBLICATIONS

Figure 2A:
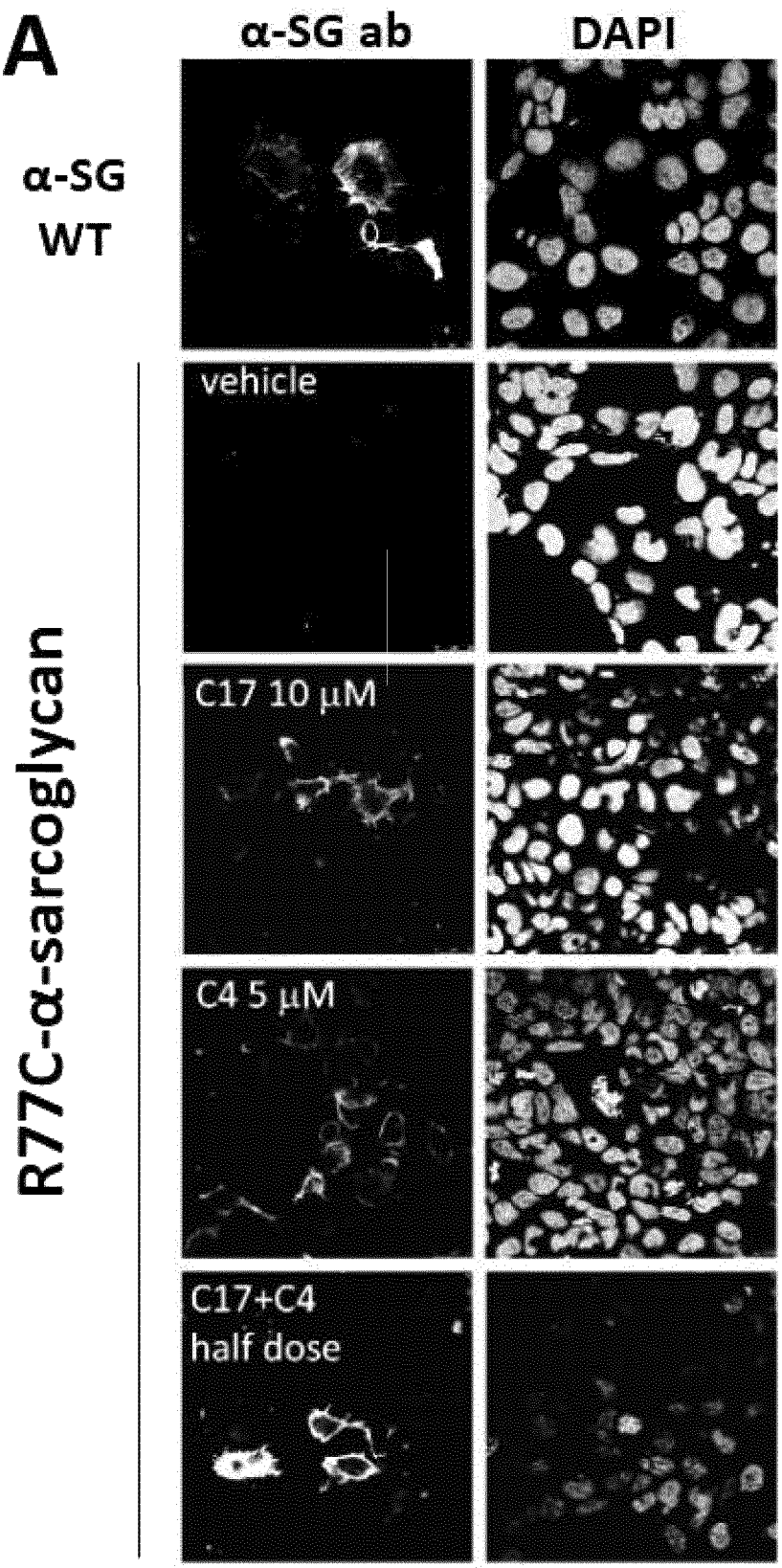

Okiyoneda et al., "Mechanism-based corrector combination restores [Delta]F508-CFTR folding and function", Nature Chemical Biology, vol. 9, No. 7, Jul. 1, 2013 (Jul. 1, 2013), pp. 444-454, XP055483624.
Sandona et al., "Sarcoglycanophathies: molecular pathogenesis and therapeutic prospects", Cambridge Core, vol. 11, p. 1-16, Jul. 2009.
Soheili et al., "Rescue of sarcoglycan mutations by in inhibition of endoplasmic reticulum quality control is associated with minimal structural modifications", Human Mutation, vol. 32, Issue 2, p. 1-5, Nov. 16, 2011.
Tarakci et al., "The Sarcoglycan Complex in Skeletal Muscle", Front Biosci (Landmark Ed.) Jan. 1, 2016;21:744-56.
Van Der Woerd et al., "Rescue of Defective ATP8B1 Trafficking by CFTR Correctors as a Therapeutic Strategy for Familial Intrahepatic Cholestasis", J Hepatol. Jun. 2016;6:4(6)1339-47.
Zhu et al., "Cellular Senescence in Human Myoblasts is Overcome by Human Telomerase Reverse Transcriptase and Cyclin-Dependent Kinase 4:Consequences in Aging Muscle and Therapeutic Strategies for Muscular Dystrophies", Aging Cell. Aug. 2007;6(4):515-23.
International Search Report issued in application No. PCT/EP2019/050585, dated Apr. 2, 2019.

\* cited by examiner

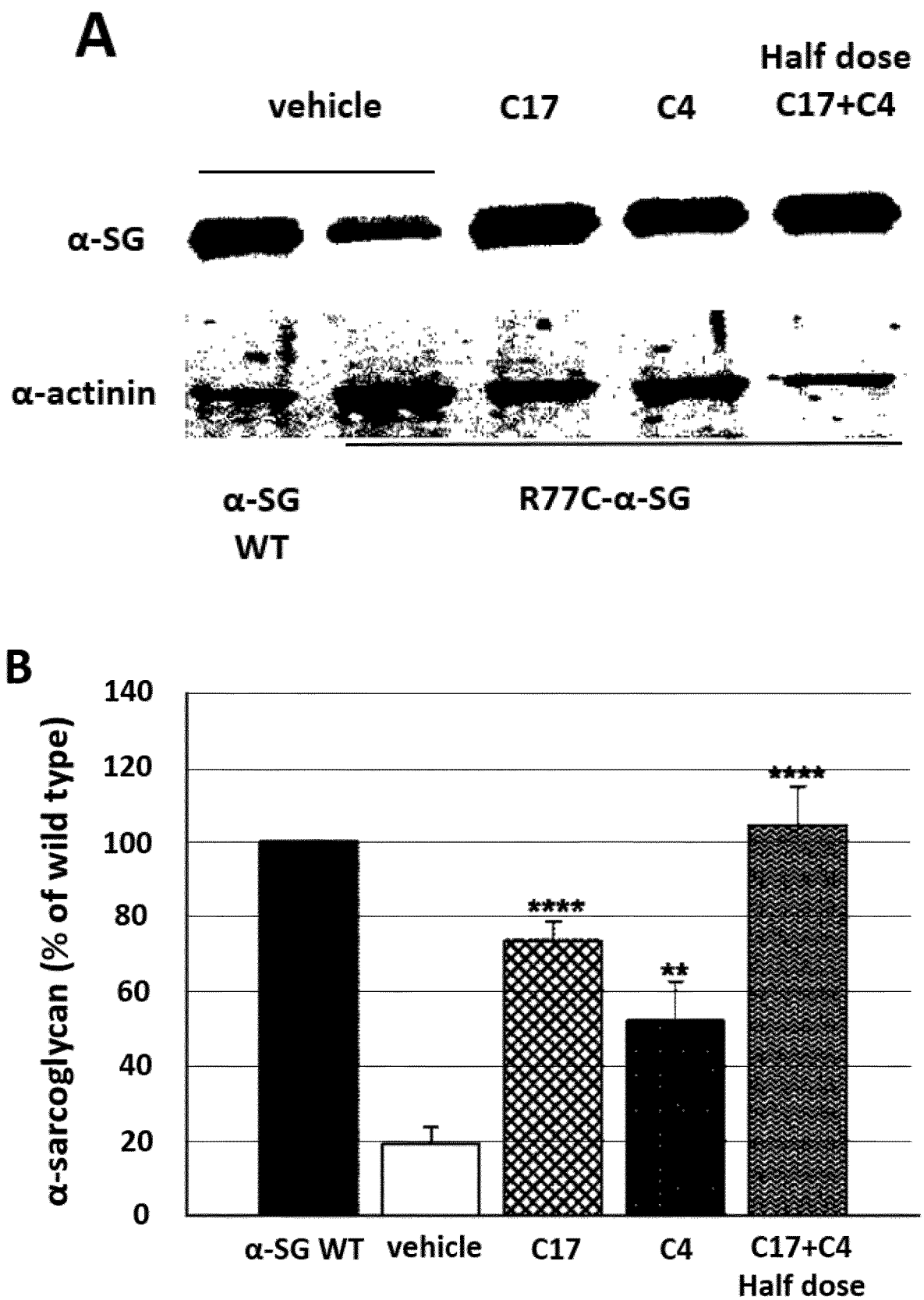
Figure 1A & B

COMBINATION TREATMENT OF SARCOGLYCANOPATHIES

CROSS-REFERENCE TO RELATED APPLICATIONS

This application is the U.S. National Phase under 35 U.S.C. § 371 of International Application PCT/EP2019/050585, filed Jan. 10, 2019, which claims the benefit of European Application No. 18305018.6, filed Jan. 11, 2018, the disclosures of which are incorporated by reference herein in their entireties.

FIELD OF THE INVENTION

The present invention relates to combination treatment of sarcoglycanopathies.

BACKGROUND OF THE INVENTION

Sarcoglycanopathies are autosomal recessive diseases caused by mutations in the one of the genes coding for any sarcoglycans (SG). SG are single-pass transmembrane glycoproteins that form a tetrameric complex localized into the sarcolemma of striated muscle (1,2). The sarcoglycan complex, as part of the dystrophin-associated protein complex (DAPC), plays a key role in assuring sarcolemma stability during muscle contraction, and seems involved in signaling processes (3). All forms of sarcoglycanopathy (LGMD2C, 2D, 2E and 2F) can be classified as Loss of Function (LOF) disease because defects in the specific sarcoglycan are typically responsible for the absence/strong reduction of the mutated protein with the secondary deficiency of the wild type partners (4). In the last few years, by studying the pathogenesis of sarcoglycanopathies, it has been established that the LOF condition is the consequence of the activity of the protein quality control (QC) system of the cell. In particular, the majority of sarcoglycanopathy genetic defects are missense mutations originating a folding-defective protein that is recognized by the Endoplasmic Reticulum-QC and delivered to degradation through the ubiquitin-proteasome system (5,6).

Moreover, different missense mutants of SG can be properly rescued at the plasma membrane, by targeting the degradative pathway (5-8). This evidence also suggests that, although mutated, these proteins retain their functionality and that the development of novel therapeutic strategies, aiming to reduce the disposal of the mutants, would be fruitful for patients. To this intent, being the presence of a folding-defective SG of the main cause of pathogenicity in sarcoglycanopathies, it is conceivable a "repair strategy" by means of small molecules facilitating the folding process of the mutants that can therefore pass the quality control and move at the proper site of action.

In this context, use of cystic fibrosis transmembrane regulator (CFTR) correctors for the treatment of sarcoglycanopathies was disclosed (WO2014086687).

SUMMARY OF THE INVENTION

The present invention relates to combination treatment of sarcoglycanopathies. In particular, the present invention is defined by the claims.

DETAILED DESCRIPTION OF THE INVENTION

Sarcoglycanopathies are autosomal recessive diseases caused by mutations in the one of the genes coding for any sarcoglycans (SG). For instance, Limb Girdle Muscular Dystrophy type 2D (LGMD2D) is a rare autosomal-recessive disease, affecting striated muscle, due to mutation of SGCA, the gene coding for α-sarcoglycan. Nowadays more than 50 different SGCA missense mutations have been reported. They are supposed to impact folding and trafficking of α-sarcoglycan because the defective polypeptide, although potentially functional, is recognized and disposed of by the quality control of the cell. The secondary reduction of α-sarcoglycan partners, β-, γ- and δ-sarcoglycan, disrupts a key membrane complex that, associated to dystrophin, contributes to assure sarcolemma stability during muscle contraction. The complex deficiency is responsible for muscle wasting and the development of a severe form of dystrophy. The inventors previously showed that the application of small molecules developed to rescue ΔF508-CFTR trafficking, and known as CFTR correctors, improved the maturation of several α-sarcoglycan mutants that were consequently rescued at the plasma membrane (WO 014086687). Now, the inventors show that some specific CFTR correctors provide additive and even synergic effect when administered in combination.

Accordingly the first object of the present invention relates to a method of treating a sarcoglycanopathy in a patient in need thereof comprising administering to the patient a therapeutically effective combination of N-(2-(5-chloro-2-methoxyphenylamino)-4'-methyl-4,5'-bithiazol-2'-yl)pivalamide (C17) and a further compound that is N-[2-(5-Chloro-2-methoxy-phenylamino)-4'-methyl-[4,5'] bithiazolyl-2'-yl]-benzamide (C4), 4,5,7-trimethyl-N-phenylquinolin-2-amine (C5), N-(4-bromophenyl)-4-methylquinolin-2-amine (C6) or N-(2-(3-acetylphenylamino)-4'-methyl-4,5'-bithiazol-2'-yl) benzamide (C13).

As used herein, the term "sarcoglycanopathy" has its general meaning in the art and refers to a muscular dystrophy resulting from mutations in any of the sarcoglycan genes. In particular, sarcoglycanopathies include LGMD-2C, LGMD-2D, LGMD-2E, and LGMD-2F.

As used herein, the term "LGMD-2C" means Limb Girdle Muscular Dystrophy type 2C (sarcoglycanopathy) caused by mutations of the SGCG gene coding for gamma-sarcoglycan.

As used herein, the term "LGMD-2D" means Limb Girdle Muscular Dystrophy type 2D (sarcoglycanopathy) caused by mutations of the SGCA gene coding for alpha-sarcoglycan. The most common defect of LGMD-2D is the missense mutation c. 229C>T/p.R77C.

As used herein, the term "LGMD-2E" means Limb Girdle Muscular Dystrophy type 2E (sarcoglycanopathy) caused by mutations of the SGCB gene coding for beta-sarcoglycan.

As used herein, the term LGMD-2F means Limb Girdle Muscular Dystrophy type 2F (sarcoglycanopathy) caused by mutations of the SGCD gene coding for delta-sarcoglycan.

As used herein, the term "treatment" or "treat" refer to therapy with respect to a patient diagnosed with a sarcoglycanopathy. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

The drugs are well known to the skilled person. For instance the preparations of C17, is fully described in WO2004111014, and the preparations of C4, C5, C6 and C13 are described in WO2006101740.

As used herein, the term "combination" is intended to refer to all forms of administration that provide a first drug together with a further (second, third . . . ) drug. The drugs may be administered simultaneous, separate or sequential and in any order. Drugs administered in combination have biological activity in the patient to which the drugs are delivered. Within the context of the invention, a combination thus comprises at least two different drugs, and wherein one drug is C17 and wherein the other drug is C4, C5, C6 or C13. According to the present invention the combination of the present invention provides additive and even synergistic effects as illustrated by the EXAMPLES. The term "synergy" or "synergistic" encompasses a more than additive effect of a combination of two or more agents compared to their individual effects. In some embodiments, synergy or synergistic effect refers to an advantageous effect of using two or more agents in combination, e.g., in a pharmaceutical composition, or in a method of treatment.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the drug are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. A therapeutically effective amount of a therapeutic compound typically ameliorate the symptoms in the patient. One of ordinary skill in the art would be able to determine such amounts based on such factors as the patient's size, the severity of the patient's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance 0.1-20 mg/kg, such as about 0.1-10 mg/kg, for instance about 0.5, about such as 0.3, about 1, about 3 mg/kg, about 5 mg/kg or about 8 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the drugs of the present invention are administered to the patient in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the patient. The compositions of the present invention may be administered orally, parenterally, by inhalation spray, or via an implanted reservoir. The used herein includes subcutaneous, intravenous, intramuscular, or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The invention will be further illustrated by the following figures and examples. However, these examples and figures should not be interpreted in any way as limiting the scope of the present invention.

FIGURES

FIG. 1: rescue of the folding-defective R77C-α-SG by the administration of CFTR correctors.

A, Western blot of protein lysates from βγδ-cells transiently expressing R77C-α-SG and treated for 24 hours with corrector C17 10 μM, C4 5 μM, or the combination of corrector C17+C4 (each one-half dose, i.e. 5 μM and 2.5 μM respectively). Cells expressing wild type-α-SG were utilized as positive control. Membrane were probed with antibodies against α-SG and α-actinin, used as loading control.

B, quantification by densitometric analysis of α-SG protein bands on at least three independent Western blot experiments. The average amount of α-SG (+/−SEM) is shown as percentage of the protein content in cells expressing the wild type form. Statistical analysis was performed by One-way ANOVA test—multiple comparisons Dunnet test , P<0.01; **P<0.0001.

FIG. 2: synergic effect of the combined administration of C17+C4 on the defective R77C-α-SG A, IF confocal analysis of βγδ-cells expressing R77C-α-SG and treated for 24 hours with vehicle or the indicated correctors. Intact cells (not permeabilized) were immunedecorated with an anti α-SG antibody, recognizing an extracellular epitope, revealed by the secondary Alexa Fluor 594-conjugated anti-mouse antibody. Cells expressing wild type-α-SG are shown as positive control. On the right of each image is reported the same field with nuclei stained by DAPI. Images were recorded with a Leica SP5 laser scanning confocal microscope at the same setting conditions and magnification.

B, Mean fluorescence intensity of membrane staining of βγδ-cells expressing R77C-α-SG treated for 24 hours with vehicle (negative control) or the indicated correctors; βγδ-cells expressing WT-α-SG were used as positive control. Fluorescence values from at least three independent experiments, performed in triplicate, were recorded by using the ImageXpress microscope system. Mean values (+/−SEM) were normalized for the number of cells positive for both α-SG and DAPI under permeabilization condition to consider transfection efficiency. Statistical analysis was performed by One-way ANOVA test—multiple comparisons Bonferroni test; n.s., P>0.05; , P<0.01; *P<0.001; ****, P<0.0001.

Figure 3:
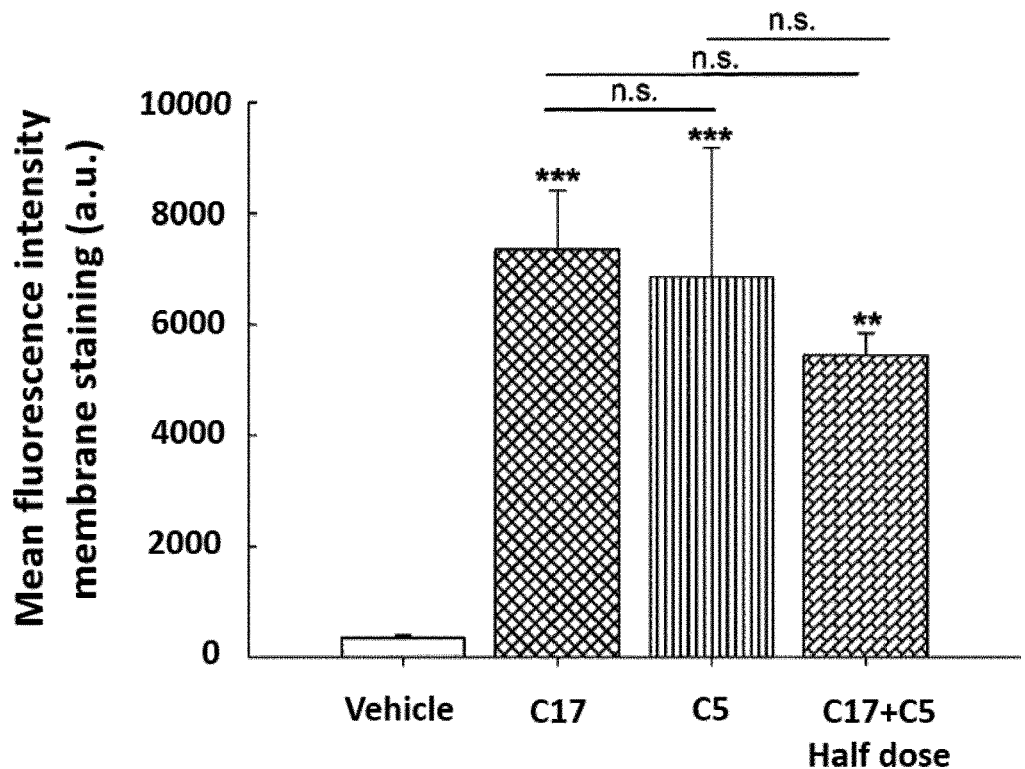

FIG. 3 additive effect of the combined administration of C17+C5 on the -defective R77C-α-SG. Mean fluorescence intensity of membrane staining of βγδ-cells expressing R77C-α-SG treated for 24 hours with vehicle (negative control), C17 10 μM, C5 5 μM or C17+C5 (each one-half dose, i.e. 5 μM and 2.5 μM, respectively). The ImageXpress microscope system was utilized to record the fluorescence values from at least 3 independent experiments, performed in triplicate. Mean values (+/−SEM) were normalized for the number of cells positive for both α-SG and DAPI under permeabilization condition to take into account transfection efficiency. Statistical analysis was performed using One-way ANOVA test—multiple comparisons Bonferroni test; n.s., P>0.05; , P<0.01; *P<0.001.

Figure 4:
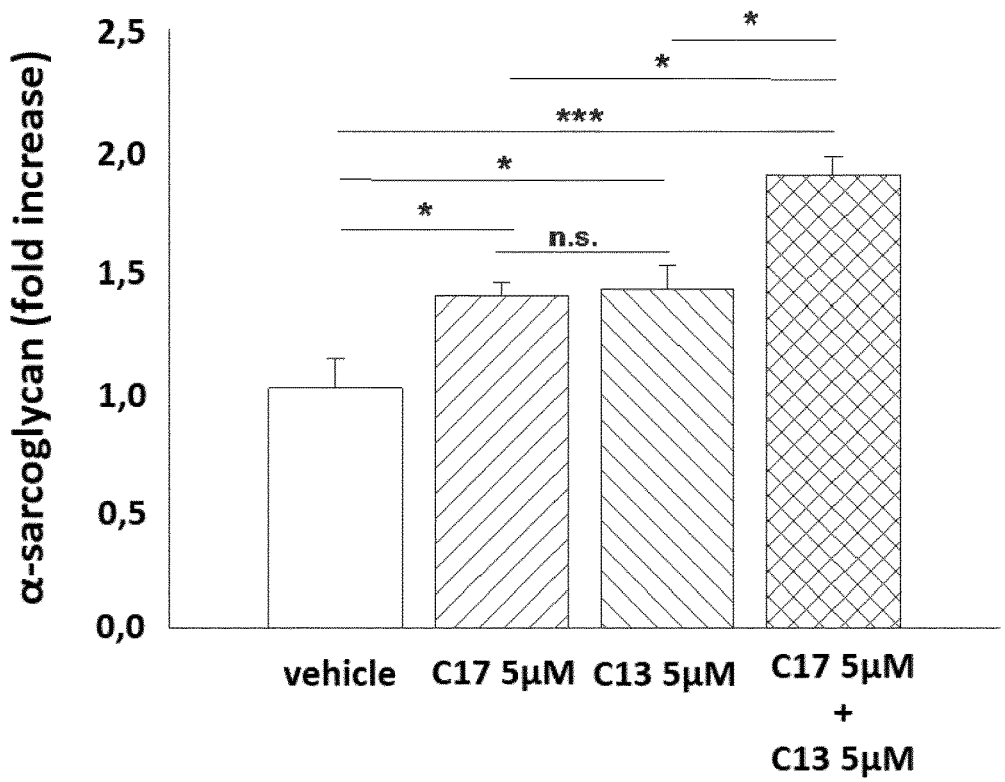

FIG. 4: additive effect of the combined administration of C17+C13 on defective α-SG in myotubes from a LGMD2D patient. Myogenic cells form a LGMD2D patient carrying the L31P and V247M mutation on the SGCA alleles were differentiated for 7 days. During the last 4 days, cells were treated with vehicle (negative control), C17 5 μM, C13 5 μM or C17+C13 (each one 5 μM). At the end of the treatments, myotubes were lysed and the content of α-SG was evaluated by western blot and densitometric analysis of at least 3 independent experiments. The average amount of α-SG (+/−SEM), is expressed as fold increase of the protein content of the negative control (vehicle). Statistical analysis was performed using One-way ANOVA test—followed by Tukey HSD Post-hoc Test; n.s., P>0.05; *, P<0.05; ***, P<0.001.

Figure 5:
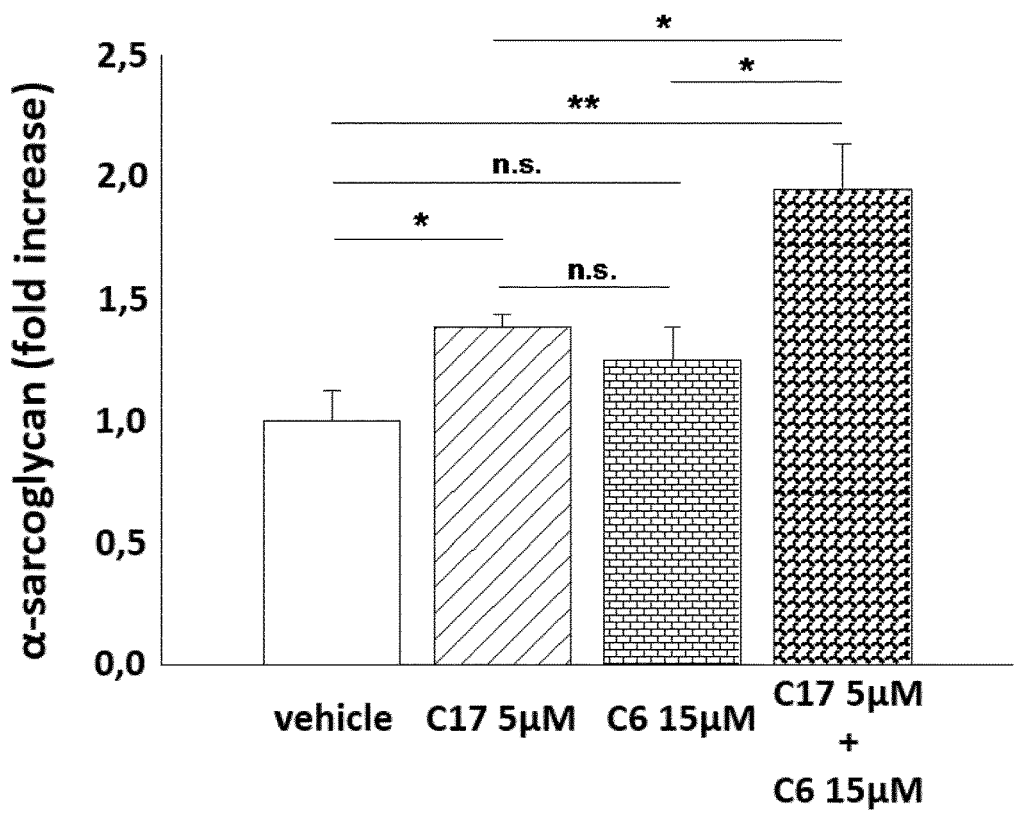

FIG. 5: additive effect of the combined administration of C17+C6 on defective α-SG in myotubes from a LGMD2D patient. Myogenic cells form a LGMD2D patient carrying the L31P and V247M mutation on the SGCA alleles were differentiated for 7 days. During the last 4 days, cells were treated with vehicle (negative control), C17 5 μM, C6 15 μM or C17+C6 (5 μM+15 μM). At the end of the treatments, myotubes were lysed and the content of α-SG was evaluated by western blot and densitometric analysis of at least 3 independent experiments. The average amount of α-SG (+/−SEM), is expressed as fold increase of the protein content of the negative control (vehicle). Statistical analysis was performed using One-way ANOVA test—followed by Tukey HSD Post-hoc Test; n.s., P>0.05; *, P<0.05; **, P<0.01.

EXAMPLE

Chemicals and Treatments

Cycloheximide, glafenine and MG132 were from Sigma-Aldrich, VX809 and VX770 were from Selleck Chemicals, C4 and C17 were a kind gift of the Cystic Fibrosis Foundation, C4, C5, C6 and C13 were from Exclusive Chemistry. All compounds were dissolved in DMSO and the working solution prepared 1000× to have the same content of vehicle (1‰) in each treatment.

Plasmids, Cell Culture, Transfection, and Treatments

The full-length cDNA encoding human α-sarcoglycan cloned in the pcDNA3 mammalian expression vector was previously described (11). Plasmids expressing missense mutants of α-sarcoglycan were previously described (6, 7)

HEK-293, V247M cells (8), HER-911 and βγδ-HER were grown in Dulbecco's modified Eagle's medium (Sigma) supplemented with 10% fetal bovine serum (FBS) (Gibco) and maintained in a humidified atmosphere containing 5% $CO_2$ at 37° C.

Immortalized human myoblasts (12) were from the "Human cell culture platform" of the Myology Institute in Paris. Primary human myogenic cells from an LGMD2D patient were isolated from a bioptic fragment from the Telethon Genetic Bio-Bank facility (8). Myogenic cells were grown in Skeletal Muscle Cell Growth Medium (Promocell) supplemented with 15% FBS (Gibco), named skeletal growth medium (SGM). To start differentiation, myoblasts grown at confluence were incubated with DMEM supplemented with 2% Horse Serum (Euroclone), 10 μg/ml human recombinant insulin (Sigma), 100 μg/ml human Apotransferrin (Sigma-Aldrich), named skeletal differentiating medium (SDM). Differentiation was carried out for seven days.

For transient expression, HEK 293 cells were seeded at 50,000 cells/cm2 and transfected the day after with Transit293 (MirusBio) according to manufacturer's instruction. Twenty-four hours after transfection, medium was replaced with DMEM supplemented with 2% FBS containing the indicated concentration of correctors (dissolved in DMSO) or with DMSO alone (final DMSO concentration 0.1%). HER911 or βγδ-cells cells were seeded at 50,000 cells/cm2 and transfected the day after with 9 μl of Fugene HD Transfection Reagent (E2312 from Promega) and 3 μg of plasmid coding for wild type or mutated α-SG. MG132 was added 8 hours before cell lysis, CFTR correctors were added 24 hours before cell lysis or IF assay (transfected HEK293, V247M cells, HER911 and βγδ-cells) and 24-96 hours before myotubes lysis, treatment with CHX or IF assay.

After treatments, cells were washed twice with ice cold PBS and lysed with 5% sodium deoxycholate supplemented with complete protease inhibitor (Sigma-Aldrich).

Establishment of a HER911 Cell Line Stably Expressing β-, γ-, and δ-Sarcoglycan

The stably expressing βγδ-SG clonal cell line was obtained by integration of β-SG, γ-SG, and δ-SG cDNA using lentiviral vectors in HER911 cells. The day following plating cells in 6-well plates, an appropriate volume of lentiviral vector-expressing β-, γ- an δ-SG was added directly into each well containing 1 ml of culture medium, to infect the cells at 100 Multiplicity of Infection (MOI). After 3 hours of incubation at 37° C., 1 ml of culture medium was added into each well and cells were incubated at 37° C. for an additional 48 hr. Each well was subcultured again in 6-well plates and the transduction was repeated two more times as explained above. After three transductions, cells were sub-cultured in a T-75 culture flask and were maintained at 37° C. until 100% of confluence. Then, cells were collected, centrifuged, and resuspended in culture medium at a density of $5\times10^5$ cells/ml. To obtain clonal cell lines, single cells were sorted by Astrios Beckman Coulter (Brea, Calif.) from the cell suspension and seeded in 96-well plates in culture medium. After 10 days, a total number of 30 clonal cell lines were selected and subcultured in larger culture plates. All 30 clones were subjected to qPCR analysis to determine the copy-number/genome of each SG and to RT-qPCR analysis to monitor the expression of SGs. One positive SG expressing cell clone was chosen for the next step.

Immunoblot Analysis

Protein lysates were quantified by the bicinchoninic-acid protein assay kit (Thermo Scientific), according to manufacturer's instructions. Proteins proteins lysates were resolved on NuPAGE® Novex® 4-12% Bis-Tris Protein Gels (Thermo Fisher Scientific) and transferred to nitrocellulose membranes (iBlot, Thermo Fisher Scientific) following the manufacturer's instructions. Membranes were blocked in Odyssey Blocking Buffer (Li-Cor) for 1 hour at room temperature. Incubations with primary antibodies (see below) were carried out at 4° C. overnight in Odyssey Blocking Buffer. After 1-hour incubation with donkey anti-rabbit IRDye680 and anti-mouse IRDye800 antibodies (EuroBio) at room temperature, proteins were detected by fluorescence in an Odissey imaging system (Li-Cor) following the manufacturer's instructions.

Densitometry was performed with the ImageJ software. The intensities of α-sarcoglycan bands were normalized for the intensity of α-actinin.

Confocal Immunofluorescence

Immunofluorescence-confocal analyses were performed either in intact cells (not permeabilized) or in permeabilized cells. For the former condition, cells, grown on polylysine-treated glasses, at the end of treatments were incubated for 30 minutes at 4° C., then gently washed twice with ice-cold PBS and incubated with primary antibodies for 5 hours at 4° C. After three gentle washings with ice-cold PBS, cells were incubated with fluorescently labeled secondary antibodies for 2 hours at 4° C. Primary and secondary antibodies were diluted in PBS supplemented with 0.5% BSA. After secondary antibody incubation, cells were washed with PBS and then fixed for 15 minutes with 4% paraformaldehyde in PBS (PFA). After incubation with 50 mmol/L $NH_4Cl$ for 15 minutes and washing with PBS, nuclei were stained with Hoechst or DAPI. For analysis in permeabilized cells, cells grown and treated as above, were washed with PBS, fixed for 15 minutes in PBS 3.7% formaldehyde (Sigma-Aldrich) at room temperature. Slides were rinsed in PBS and permeabilized with PBS 0.5% Triton X-100 (Sigma-Aldrich) for 5 min and then blocked for 30 min with PBS containing 10% SVF to prevent non-specific staining. Incubation with primary and secondary antibody was performed as above described. Cells were examined with a Leica SP5 confocal laser scanning microscope.

Quantification of the mean fluorescence intensity of membrane staining of ↑γδ-cells transfected with R77C-α-SG was performed by using ImageXpress microscope system (Molecular Devices). Normalization was performed by counting the number of cells positive for both DAPI and α-SG in permeabilization conditions to consider possible differences in transfection efficiency.

Antibodies

Mouse monoclonal antibody specific for α-SG (NCL-α-SARC) was from Leica Biosystem; rabbit polyclonal antibody specific for α-actinin was from Santa Cruz. Alexa fluor 488, Alexa fluor 594- and DyLight 488-conjugated goat anti-mouse and goat anti-rabbit were from Life Technologies.

Statistical Analysis

Data are expressed as means+/−SEM. Statistical differences among groups were determined by One-way ANOVA test, followed by either Dunnett test for simultaneous multiple comparisons with control, or Bonferroni test for simultaneous comparisons of all possible contrasts (pairs). A level of confidence of $P<0.05$ was used for statistical significance.

Results

Figure 2B:
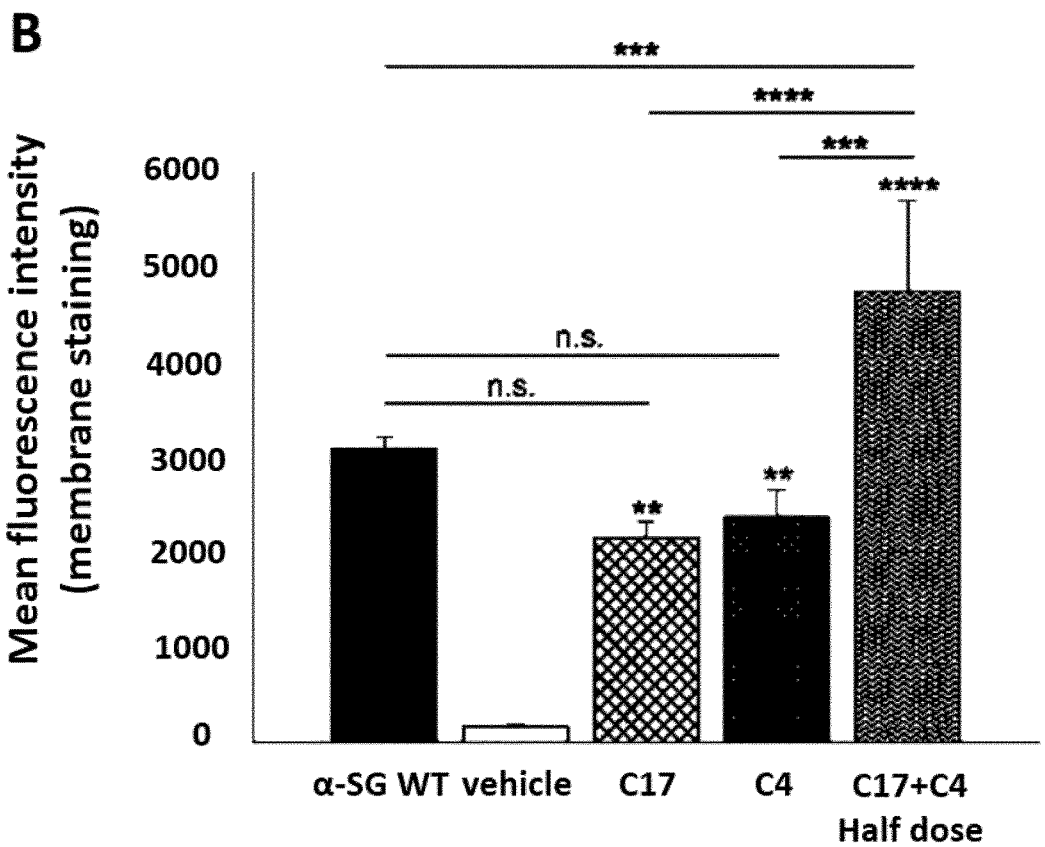

The R77C amino acid substitution is the most frequently reported mutation responsible for LGMD2D [http://www.dmd.nl] This mutant tends to aggregate when expressed alone, therefore it was established a cell line, hereafter named βγδ-cells, in which the cDNAs coding for the wild type β-, γ-, δ-SG were stably integrated in the genome of HER911 cells by lentivirus transduction (data not shown). The subsequent transfection with either wild type or R77C-α-SG led to the production of the final cell model. The level of R77C-α-SG transfected in βγδ-cells (either untreated or treated with the sole vehicle) is very low, about 20% in comparison to wild type (FIGS. 1A and B) and the protein was almost undetectable at the plasma membrane (FIG. 2A, vehicle), well mimicking the condition present in patient's muscle cells (9, 10). This model was utilized to assess the efficacy of CFTR correctors C17 and C4, administered either as single molecule or in combination. Treatment with C17 and C4 induced a three to four-fold increase of R77C-α-SG protein content (FIGS. 1A and B). Remarkably, the rescued protein localized at the plasma membrane, as proven by the intense cell-surface staining of not-permeabilized cells (FIG. 2A). Notably, the combined C17+C4 administration, each corrector at half dose of the single application, resulted in a more robust effect, as the total mutant content reached that of the wild type (FIG. 1B). In addition, the intensity of the fluorescence signal at the plasma membrane was significantly higher than the one obtained by individually applied correctors (FIG. 2B), as evaluated by using the ImageXpress microscope system. We then tested the co-administration of corrector C5 with corrector C17, again at halved dose compared with the single administration. Also in this case the combination of correctors resulted in the additional increase of the cell surface α-SG rescue in comparison to the single-compound administration (FIG. 3). We also tested the co-administration of corrector C6 with corrector C17 and corrector C13 with corrector C17 (FIGS. 4 and 5). Also in these cases, the combination of correctors resulted in the additional increase of the cell surface α-SG rescue in comparison to the single-compound administration. All this considered, we conclude that mutants of sarcoglycans, such as R77C-α-SG, can be successfully rescued in vitro by CFTR corrector treatments and that correctors may have an additive and even synergic effect when administered in combination.

REFERENCES

Throughout this application, various references describe the state of the art to which this invention pertains. The disclosures of these references are hereby incorporated by reference into the present disclosure.

1. Nigro, V. and Savarese, M. (2014) Genetic basis of limb-girdle muscular dystrophies: the 2014 update. Acta Myol. 33, 1-12
2. Tarakci, H. and Berger, J. (2016) The sarcoglycan complex in skeletal muscle. Front. Biosci. (Landmark Ed.). 21, 744-756
3. Sandoná, D. and Betto, R. (2009) Sarcoglycanopathies: molecular pathogenesis and therapeutic prospects. Expert Rev. Mol. Me. 11, e28
4. Kirschner, J. and Lochmiiller, H. (2011) Sarcoglycanopathies. Handb. Clin. Neurol. 101,141
5. Barton, M., Gicquel, E., Barrault, L., Soheili, T., Malissen, M., Malissen, B., Vincent-Lacaze, N., Perez, N., Udd, B., Danos, O. and Richard, I. (2008) Mannosidase I inhibition rescues the human alpha-sarcoglycan R77C recurrent mutation. Hum. Mol. Genet. 17, 1214-1221
6. Gastaldello, S., D'Angelo, S., Franzoso, S., Fanin, M., Angelini, C., Betto, R. and Sandona, D. (2008) Inhibition of proteasome activity promotes the correct localization of disease-causing alpha-sarcoglycan mutants in HEK-293 cells constitutively expressing beta-, gamma-, and delta-sarcoglycan. Am. J. Pathol. 173, 170-181
7. Soheili, T., Gicquel, E., Poupiot, J., N'Guyen, L., Le Roy, F., Bartoli, M. and Richard, I. (2012) Rescue of sarcoglycan mutations by inhibition of endoplasmic reticulum quality control is associated with minimal structural modifications. Hum. Mutat. 33, 429-439
8. Bianchini, E., Fanin, M., Mamchaoui, K., Betto, R. and Sandona, D. (2014) Unveiling the degradative route of the V247M α-sarcoglycan mutant responsible for LGMD-2D. Hum. Mol. Genet. 23, 3746-3758
9. Carrie, A., Piccolo, F., Leturcq, F., de Toma, C., Azibi, K., Beldjord, C., Vallat, J. M., Merlini, L., Voit, T., Sewry, C., et al (1997) Mutational diversity and hot spots in the alpha-sarcoglycan gene in autosomal recessive muscular dystrophy (LGMD2D). J. Med. Genet. 34, 470-475
10. Duggan, D. J., Gorospe, J. R., Fanin, M., Hoffman, E. P. and Angelini, C. (1997) Mutations in the sarcoglycan genes in patients with myopathy. N. Engl. J. Med. 336, 618-624
11. van der Woerd, W. L., Wichers, C. G., Vestergaard, A. L., Andersen, J. P., Paulusma, C. C., Houwen, R. H. and van de Graaf, S. F. (2016) Rescue of defective ATP8B1 trafficking by CFTR correctors as a therapeutic strategy for familial intrahepatic cholestasis. J. Hepatol. 64, 1339-1347
12. Zhu, C. H., Mouly, V., Cooper, R. N., Mamchaoui, K., Bigot, A., Shay, J. W., Di Santo, J. P., Butler-Browne, G. S. and Wright, W. E. (2007) Cellular senescence in human myoblasts is overcome by human telomerase reverse transcriptase and cyclin-dependent kinase 4: consequences in aging muscle and therapeutic strategies for muscular dystrophies. Aging Cell 6, 515-523

The invention claimed is:

1. A method of treating a sarcoglycanopathy in a patient in need thereof comprising administering to the patient a therapeutically effective combination of N-(2-(5-chloro-2-methoxyphenylamino)-4'-methyl-4,5'-bithiazol-2'-yl)pivalamide (C17) and a further compound that is selected from the group consisting of N-[2-(5-Chloro-2-methoxy-phenylamino)-4'-methyl-[4,5']bithiazolyl-2'-yl]-benzamide (C4), 4,5,7-trimethyl-N-phenylquinolin-2-amine (C5), N-(4-bromophenyl)-4-methylquinolin-2-amine (C6) and N-(2-(3-acetylphenylamino)-4'-methyl-4,5'-bithiazol-2'-yl)benzamide (C13).

2. The method of claim 1 wherein the sarcoglycanopathy is selected from the group consisting of Limb Girdle Muscular Dystrophy type 2D (LGMD-2D), LGMD-2E, LGMD-2C or LGMD-2F.

3. The method of claim 1 wherein the sarcoglycanopathy is LGMD-2D.

4. The method of claim 3 wherein the sarcoglycanopathy is LGMD-2D caused by a c. 229C>T/p.R77C mutation.

* * * * *